(12) United States Patent
Berlin et al.

(10) Patent No.: US 7,465,578 B2
(45) Date of Patent: Dec. 16, 2008

(54) NUCLEIC ACID SEQUENCING BY RAMAN MONITORING OF UPTAKE OF PRECURSORS DURING MOLECULAR REPLICATION

(75) Inventors: Andrew Berlin, San Jose, CA (US); Steven J. Kirch, Pleasanton, CA (US); Gabi Neubauer, Los Gatos, CA (US); Valluri Rao, Saratoga, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 429 days.

(21) Appl. No.: 10/886,094

(22) Filed: Jul. 7, 2004

(65) Prior Publication Data

US 2004/0248185 A1 Dec. 9, 2004

Related U.S. Application Data

(62) Division of application No. 09/962,288, filed on Sep. 24, 2001, now Pat. No. 6,852,492.

(51) Int. Cl.
*C12M 1/00* (2006.01)
*C12M 3/00* (2006.01)
*G01J 3/44* (2006.01)
*C12Q 1/68* (2006.01)
*C12P 19/34* (2006.01)
*C07H 21/02* (2006.01)
*C07H 21/04* (2006.01)

(52) U.S. Cl. ............. 435/283.1; 435/287.2; 435/287.9; 435/288.7; 435/6; 435/91.2; 536/23.1

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,962,037 A | 10/1990 | Jett et al. | |
| 5,038,853 A | 8/1991 | Callaway et al. | |
| 5,126,022 A | 6/1992 | Soane et al. | |
| 5,171,132 A | 12/1992 | Miyazaki et al. | |
| 5,271,724 A | 12/1993 | Van Lintel | |
| 5,277,556 A | 1/1994 | Van Lintel | |
| 5,306,403 A | 4/1994 | Vo-Dinh | |
| 5,401,411 A | 3/1995 | Andersson | |
| 5,405,747 A | 4/1995 | Jett et al. | |
| 5,405,766 A | 4/1995 | Kallury et al. | |
| 5,603,872 A | 2/1997 | Margalit | |
| 5,610,287 A | 3/1997 | Nikiforov et al. | |
| 5,674,743 A | 10/1997 | Ulmer | |
| 5,705,018 A | 1/1998 | Hartley | |
| 5,707,804 A | 1/1998 | Mathies et al. | |
| 5,721,102 A | 2/1998 | Vo-Dinh | |
| 5,776,674 A | 7/1998 | Ulmer | |
| 5,783,389 A | 7/1998 | Vo-Dinh | |
| 5,814,454 A | 9/1998 | Ju | |
| 5,814,516 A | 9/1998 | Vo-Dinh | |
| 5,866,336 A | 2/1999 | Nazarenko et al. | |
| 5,867,266 A | 2/1999 | Craighead | |
| 5,919,622 A | 7/1999 | Macho et al. | |
| 5,986,076 A | 11/1999 | Rothschild et al. | |
| 6,002,471 A | 12/1999 | Quake | |
| 6,017,742 A * | 1/2000 | Takenishi et al. | ........... 435/180 |
| 6,054,263 A | 4/2000 | Danssaert et al. | |
| 6,090,589 A | 7/2000 | Dimond et al. | |
| 6,127,120 A | 10/2000 | Graham et al. | |
| 6,136,543 A | 10/2000 | Anazawa et al. | |
| 6,140,053 A | 10/2000 | Koster | |
| 6,174,677 B1 * | 1/2001 | Vo-Dinh | ........................ 435/6 |
| 6,180,372 B1 | 1/2001 | Franzen et al. | |
| 6,197,503 B1 | 3/2001 | Vo-Dinh et al. | |
| 6,210,896 B1 | 4/2001 | Chan | |
| 6,214,246 B1 | 4/2001 | Craighead | |
| 6,225,068 B1 | 5/2001 | Wolfrum | |
| 6,232,075 B1 | 5/2001 | Williams | |
| 6,852,492 B2 * | 2/2005 | Berlin et al. | .................... 435/6 |
| 6,943,892 B2 * | 9/2005 | Chan | ......................... 356/479 |
| 6,982,165 B2 * | 1/2006 | Yamakawa et al. | ............ 435/6 |
| 7,056,661 B2 | 6/2006 | Korlach et al. | |
| 2002/0102595 A1 * | 8/2002 | Davis | ........................... 435/6 |
| 2005/0287536 A1 * | 12/2005 | Kozlay | ......................... 435/6 |

FOREIGN PATENT DOCUMENTS

WO WO-94/05414 3/1994

(Continued)

OTHER PUBLICATIONS

Kneipp, K. et al., Applied Spectroscopy, vol. 48, pp. 951-955 (1994).*

(Continued)

*Primary Examiner*—Teresa E Strzelecka
(74) *Attorney, Agent, or Firm*—Darby & Darby PC

(57) ABSTRACT

The methods, compositions and apparatus disclosed herein are of use for nucleic acid sequence determination. The methods involve isolation of one or more nucleic acid template molecules and polymerization of a nascent complementary strand of nucleic acid, using a DNA or RNA polymerase or similar synthetic reagent. As the nascent strand is extended one nucleotide at a time, the disappearance of nucleotide precursors from solution is monitored by Raman spectroscopy or FRET. The nucleic acid sequence of the nascent strand, and the complementary sequence of the template strand, may be determined by tracking the order of incorporation of nucleotide precursors during the polymerization reaction. Certain embodiments concern apparatus comprising a reaction chamber and detection unit, of use in practicing the claimed methods. The methods, compositions and apparatus are of use in sequencing very long nucleic acid templates in a single sequencing reaction.

7 Claims, 1 Drawing Sheet

FOREIGN PATENT DOCUMENTS

| | | |
|---|---|---|
| WO | WO-99/44045 | 9/1999 |
| WO | WO-00/70073 | 11/2000 |
| WO | WO-01/16375 | 3/2001 |

OTHER PUBLICATIONS

Thomas, G.J. et al., J. Mol. Biol., vol. 102, pp. 103-124 (1976).*
Cotton, T. et al., J. Raman Spectr., vol. 22, pp. 729-742 (1991).*
Vo-Dinh, T., Trends Anal. Chem., vol. 17, pp. 557-582 (1998).*
Zhang, X. et al., J. Am. Chem. Soc., vol. 127, pp. 4484-4489 (2005).*
InspectroRamanTM brochure from DeltaNu (downloaded from www.deltanu.com Jun. 6, 2008).*
Kneipp, K. et al., "Near-Infrared Surface-enhanced Raman Scattering (NIR SERS) on Colloidal Silver and Gold", Applied Spectroscopy, vol. 48, pp. 951-955 (1994).*
Cotton, T. M. et al., "Application of Surface-Enhanced Raman Spectroscopy to Biological Systems", J. Raman Spectroscopy, vol. 22, pp. 729-742 (1991).*
Thomas, G. J. Jr et al., "Studies of Virus Structure by Laser-Raman Spectroscopy", J. Mol. Biol., vol. 102, pp. 103-124 (1976).*
Vo-Dinh, T. et al., "Surface-Enhanced Raman Gene Probes", Anal. Chem., vol. 66, pp. 3379-3383 (1994).*
Syvanen, A.-C., "Detection of sequence variation using primer extension", in "Mutation Detection. A Practical Approach", Cotto R.G.H., editor, Oxford University Press (1998).*
Benevides and Thomas. (1983). "Characterization of DNA structures by Raman spectroscopy: high-salt and low-salt forms of double helical poly(dG-dC) in H20 and D20 solutions and applications to B, Z, and A-DNA," *Nucleic Acids Research* 11(16):5747-5761.
Berger and Kimmel, eds. (1987). *Methods in Enzymologist vol. 152: Guide to Molecular Cloning Techniques*. Academic Press, Inc.: New York, NY, v-x Table of Contents.
Craighead, H.G. (2000). "Nanoelectromechanical Systems," *Science* 290:1532-1535.
Goodman and Tippin. (2000). "The Expanding Polymerase Universe," *National Review of Molecular Cell Biology* 1:101-109.
Goodwin et al. (1996). "Single-Molecule Detection in Liquids by Laser-Induced Fluorescence," *Acc. Chem. Res.* 29:607-613.
Graham et al. (2000). "Detection and Identification of Labeled DNA by Surface Enhanced Resonance Raman Scattering," *Biopolymers (Biospectroscopy)* 57:85-91.
Holstrøm et al. (1993). "A Highly Sensitive and Fast Nonradioactive Method for Detection of Polymerase Chain Reaction Products," *Analytical Biochemistry* 209:278-283.
Ju et al. (1995). "Fluorescence energy transfer dye-labeled primers for DNA sequencing and analysis," *Procedures of the National Academy of Sciences of USA* 92:4347-4351.
Mansy and Peticolas. (1976). "Detection of the Sites of Alkylation in DNA and Polynucleotides by Laser Raman Spectroscopy," *Biochemistry* 15(12):2650-2655.
Nampalli et al. (2001). "Fluorescence Resonance Energy Transfer Dye Nucleotide Terminators: A New Synthetic Approach for High-Throughput DNA Sequencing," *Nucleosides, Nucleotides, & Nucleic Acids* 20(4-7):361-367.
Neoh et al. (1999). "Rapid detection of the factor V Leiden (1691 G>A) and haemochromatosis (845G>A) mutation by fluorescence resonance energy transfer (FRET) and real time PCR," *Journal of Clinical Pathology* 52:766-769.
Newton et al. (1993). "The production of PCR products with 5' single-stranded tails using primers that incorporate novel phosphoramidite intermediates," *Nucleic Acids Research* 21(5):1115-1162.
Ni et al. (1990). "Flow Injection Analysis and Real-Time Detection of RNA Bases by Surface-Enhanced Raman Spectroscopy," *Anal. Chem.* 62:1958-1963.
Rao et al. (2001). "Four Color Fret Dye Nucleotide Terminators for DNA Sequencing," *Nucleosides, Nucleotides, & Nucleic Acids* 20(4-7):673-676.
Rasmussen et al. (1991). "Covalent Immobilization of DNA onto Polystyrene Microwells: The Molecules are only Bound to the 5' Side," *Analytical Biochemistry* 198:138-142.
Richter et al. (1991). "A micromachined electrohydrodynamic (EHD) pump," *Sensors and Actuators* A 29:159-168.
Running and Urdea. (1990). "A Procedure for Productive Coupling of Synthetic Oligonucleotides to Polystyrene Microtiter Wells for Hybridization Capture," *BioTechniques* 6(3):276-277.
Russell et al. (1995). "Design and Performance of an Ultraviolet Resonance Raman Spectrometer for Proteins and Nucleic Acids," *Biophysical Journal* 68:1607-1612.
Sambrook et al. eds. (1989). *Molecular Cloning: A Laboratory Manual*. Cold Spring Harbor Laboratory Press: Cold Spring Harbor, NY, xi-xxxviii Table of Contents.
Szöllösi et al. (1998). "Application of Fluorescence Resonance Energy Transfer in the Clinical Laboratory: Routine and Research," *Cytometry (Communications in Clinical Cytometry)* 34:159-179.
Furey et al. (1998). "Use of Fluorescence Resonance Energy Transfer to Investigate the Conformation of DNA Substrates Bound to the Klenow Fragment," *Biochemistry* 37:2979-2990.
Machara, N. et al., Efficient Detection of Single Molecules Eluting Off an Optically Trapped Microsphere, *Bioimaging* 6 (1998), 33-42, 1998.

* cited by examiner

NUCLEIC ACID SEQUENCING BY RAMAN MONITORING OF UPTAKE OF PRECURSORS DURING MOLECULAR REPLICATION

CROSS REFERENCE TO RELATED APPLICATIONS

This application is a divisional application of U.S. Ser. No. 09/962,288, filed Sep. 24, 2001, now U.S. Pat. No. 6,852,492, issued Feb. 8, 2005. The disclosure of the prior application is considered part of and is incorporated by reference in the disclosure of this application.

FIELD OF THE INVENTION

The present methods, compositions and apparatus relate to the fields of molecular biology and genomics. More particularly, the disclosed methods, compositions and apparatus concern nucleic acid sequencing.

BACKGROUND

The advent of the human genome project required that improved methods for sequencing nucleic acids, such as DNA (deoxyribonucleic acid) and RNA (ribonucleic acid), be developed. Genetic information is stored in the form of very long molecules of DNA organized into chromosomes. The twenty-three pairs of chromosomes in the human genome contain approximately three billion bases of DNA sequence. This DNA sequence information determines multiple characteristics of each individual, such as height, eye color and ethnicity. Many common diseases, such as cancer, cystic fibrosis, sickle cell anemia and muscular dystrophy are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. RNA, an intermediary molecule required for processing of genetic information, can also be sequenced in some cases to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming.

BRIEF DESCRIPTION OF THE DRAWINGS

The following drawings form part of the present specification and are included to further demonstrate certain embodiments. Those embodiments may be better understood by reference to one or more of these drawings in combination with the detailed description of specific embodiments presented herein.

DESCRIPTION OF ILLUSTRATIVE EMBODIMENTS

Figure 1:
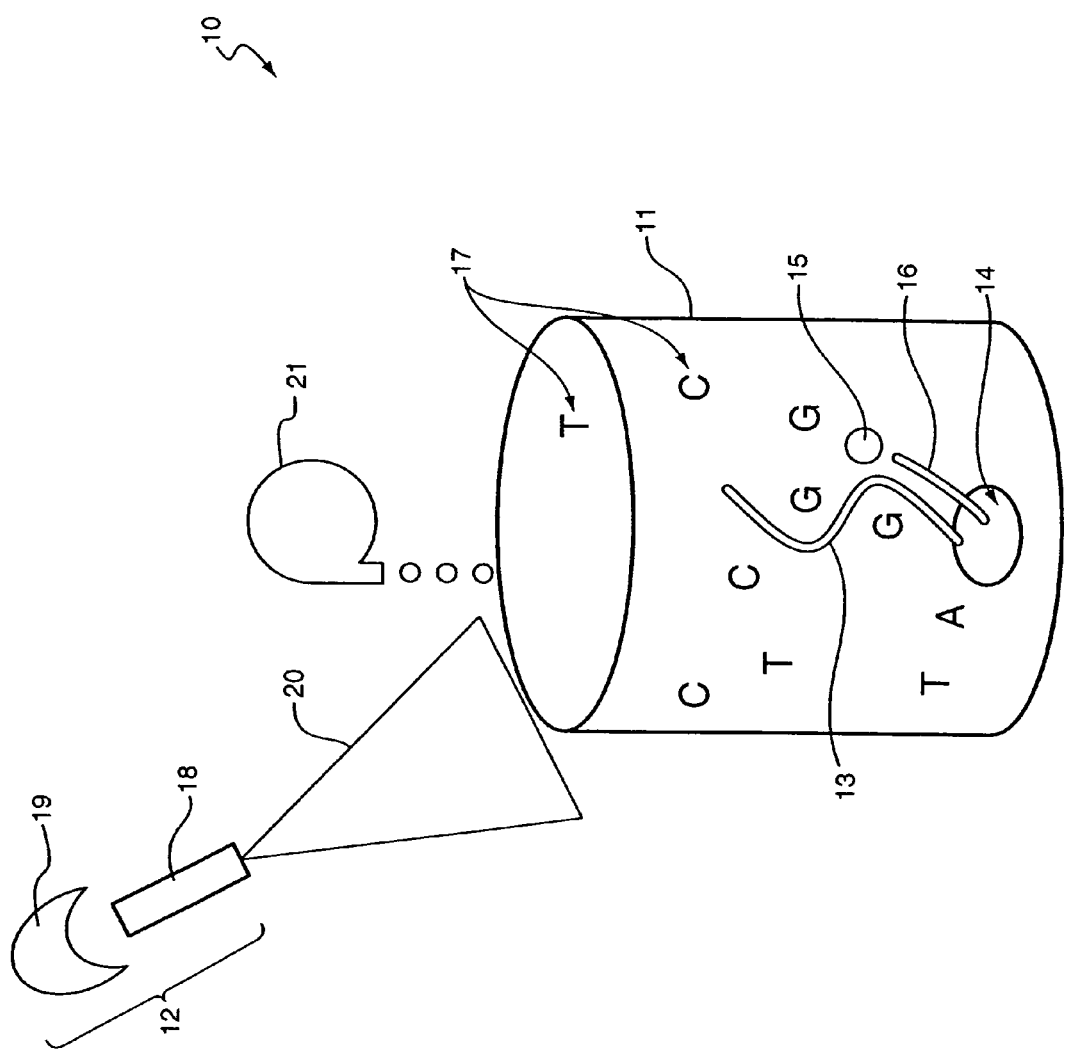
FIG. 1 illustrates an exemplary apparatus 10 (not to scale) and method for DNA sequencing in which a nucleic acid 13 is sequenced by monitoring the uptake of nucleotide precursors 17 from solution during nucleic acid synthesis.

The disclosed methods, compositions and apparatus are of use for the rapid, automated sequencing of nucleic acids 13. In particular embodiments, the methods, compositions and apparatus are suitable for obtaining the sequences of very long nucleic acid 13 molecules of greater than 1,000, greater than 2,000, greater than 5,000, greater than 10,000 greater than 20,000, greater than 50,000, greater than 100,000 or even more bases in length. In various embodiments, such sequence information may be obtained during the course of a single sequencing run, using one molecule of template nucleic acid 13. In other embodiments, multiple copies of the template nucleic acid molecule 13 may be sequenced in parallel or sequentially to confirm the nucleic acid 13 sequence or to obtain complete sequence data. In alternative embodiments, both the template strand 13 and its complementary strand may be sequenced to confirm the accuracy of the sequence information. Advantages over prior methods of nucleic acid 13 sequencing include the ability to read long nucleic acid 13 sequences in a single sequencing run, greater speed of obtaining sequence data, decreased cost of sequencing and greater efficiency in terms of the amount of operator time required per unit of sequence data generated.

In certain embodiments, the nucleic acid 13 to be sequenced is DNA, although it is contemplated that other nucleic acids 13 comprising RNA or synthetic nucleotide analogs could be sequenced as well. The following detailed description contains numerous specific details in order to provide a more thorough understanding of the disclosed embodiments. However, it will be apparent to those skilled in the art that the embodiments may be practiced without these specific details. In other instances, those devices, methods, procedures, and individual components that are well known in the art have not been described in detail herein.

Certain embodiments are illustrated in FIG. 1. FIG. 1 shows an apparatus 10 for nucleic acid 13 sequencing comprising a reaction chamber 11 and a detection unit 12. The reaction chamber 11 contains a nucleic acid (template) molecule 13 attached to an immobilization surface 14 along with a synthetic reagent 15, such as a DNA polymerase. A primer molecule 16 that is complementary in sequence to the template molecule 13 is allowed to hybridize to the template molecule 13. Nucleotide precursors 17 are present in solution in the reaction chamber 11. For synthesis of a nascent DNA strand 16, the nucleotide precursors 17 must include at least one molecule each of deoxyadenosine-5'-triphosphate (dATP), deoxyguanosine-5'-tphosphate (dGTP), deoxycytosine-5'-triphosphate (dCTP) and deoxythymidine-5'-triphosphate (dTTP). For synthesis of a nascent RNA strand 16, the nucleotide precursors 17 must comprise ATP, CTP, GTP and uridine-5'-triphosphate (UTP).

To initiate a sequencing reaction, the polymerase 15 adds one nucleotide precursor molecule 17 at a time to the 3' end of the primer 16, elongating the primer molecule 16. As the primer molecule 16 is extended, it is referred to as a nascent strand 16. For each round of elongation, a single nucleotide precursor 17 is incorporated into the nascent strand 16.

Because incorporation of nucleotide precursors 17 is determined by Watson-Crick base pair interactions with the template strand 13, the sequence of the growing nascent strand 16 will be complementary to the sequence of the template strand 13. In Watson-Crick base pairing, an adenosine (A) residue on one strand is always paired with a thymidine (T) residue on the other strand, or a uridine (U) residue if the strand is RNA. Similarly, a guanosine (G) residue on one strand is always paired with a cytosine (C) residue on the other strand. Thus, the sequence of the template strand 13 may be determined from the sequence of the nascent strand 16.

FIG. 1 illustrates embodiments in which a single nucleic acid molecule 13 is contained in a single reaction chamber 11. In alternative embodiments, multiple nucleic acid molecules 13, each in a separate reaction chamber 11, may be sequenced simultaneously. In such cases, the nucleic acid template 13 in each reaction chamber 11 may be identical or may be different. In other alternative embodiments, two or more template nucleic acid molecules 13 may be present in a single reaction chamber 11. In such embodiments, the nucleic acid molecules 13 will be identical in sequence. Where more than one template nucleic acid 13 is present in the reaction chamber 11, the Raman emission signals will represent an average of the nucleic acid precursors 17 incorporated into all nascent strands 16 in the reaction chamber 11. The skilled artisan will be able to correct the signal obtained at any given time for synthetic reactions that either lag behind or precede the majority of reactions occurring in the reaction chamber 11, using known data analysis techniques.

The skilled artisan will realize that depending on the polymerase molecule 15 used, the nascent strand 16 may contain some percentage of mis-matched bases, where the newly incorporated base is not correctly hydrogen bonded with the corresponding base in the template strand 13. In various embodiments, an accuracy of at least 90%, at least 95%, at least 98%, at least 99%, at least 99.5%, at least 99.8%, at least 99.9% or higher may be observed. The skilled artisan will be aware that certain polymerases 15 have an error correction activity (also referred to as a 3' exonuclease or proof-reading activity) that acts to remove a newly incorporated nucleotide precursor 17 that is incorrectly base-paired to the template strand 13. In various embodiments, polymerases 15 with or without a proof-reading activity may be employed. The skilled artisan will also be aware that certain polymerases 15, such as reverse transcriptase, have an inherently high error rate, allowing frequent incorporation of mismatched bases. Depending on the embodiment, a polymerase 15 with either a higher or a lower inherent error rate may be selected. In certain embodiments, a polymerase 15 with the lowest possible error rate may be used. Polymerase 15 error rates are known in the art.

The detection unit 12 comprises an excitation source 18, such as a laser, and a Raman spectroscopy detector 19. The excitation source 18 illuminates the reaction chamber 11 with an excitation beam 20. The excitation beam 20 interacts with the nucleotide precursors 17, resulting in the excitation of electrons to a higher energy state. As the electrons return to a lower energy state, they emit a Raman emission signal that is detected by the Raman detector 19. Because the Raman emission signal from each of the four types of nucleotide precursor 17 can be distinguished, the detection unit 12 is capable of measuring the amount of each type of nucleotide precursor 17 in the reaction chamber 11.

The incorporation of nucleotide precursors 17 into the growing nascent strand 16 results in a depletion of nucleotide precursors 17 from the reaction chamber 11. In order for the synthetic reaction to continue, a source of fresh nucleotide precursors 17 may be required. This source is shown in FIG. 1 as a molecule dispenser 21. In alternative embodiments, a molecule dispenser 21 may or may not be part of the sequencing apparatus 10.

In certain embodiments, the molecule dispenser 21 is designed to release each of the four nucleotide precursors 17 in equal amounts, calibrated to the rate of synthesis of the nascent strand 16. However, nucleic acids 13 do not necessarily exhibit a uniform distribution of A, T, G and C residues. In particular, certain regions of DNA molecules may be either AT rich or GC rich, depending on the species from which the DNA is obtained and the specific region of the DNA molecule being sequenced. In alternative embodiments, the release of nucleotide precursors 17 from the molecule dispenser 21 is controlled, so that relatively constant concentrations of each type of nucleotide precursor 17 are maintained in the reaction chamber 11. Such embodiments may utilize an information processing and control system that interfaces between the detection unit 12 and the molecule dispenser 21.

In embodiments involving an information processing and control system, such as a computer or microprocessor attached to or incorporating a data storage unit, data may be collected from a detector 19, such as a spectrometer or a monochromator array. The information processing and control system may maintain a database associating specific Raman signatures with specific nucleotide precursors 17. The information processing and control system may record the signatures detected by the detector 19 and may correlate those signatures with the signatures of known nucleotide precursors 17. The information processing and control system may also maintain a record of nucleotide precursor 17 uptake that indicates the sequence of the template molecule 13. The information processing and control system may also perform standard procedures known in the art, such as subtraction of background signals.

In embodiments involving a molecule dispenser 21, the addition of nucleotide precursors 17 to the reaction chamber 11, simultaneously with the incorporation of nucleotide precursors 17 into the nascent strand 16 may result in a complex Raman signal. In particular embodiments, the synthetic reaction may be allowed to run to completion or close to completion before additional nucleotide precursors 17 are added to the reaction chamber 11. In alternative embodiments, the addition of nucleotide precursors 17 to the reaction chamber 11 may occur simultaneously with incorporation of nucleotide precursors 17 into the nascent strand 16. In such embodiments, the information processing and control system may be used to correct the data on nucleotide precursor 17 concentration obtained from the Raman emission spectrum for the amount of nucleotide precursors 17 added by the molecule dispenser 21.

In certain embodiments, the reaction chamber 11 may contain a single molecule of each type of nucleotide precursor 17. In such embodiments, the release of nucleotide precursors 17 from the molecule dispenser 21 may be tightly linked to the incorporation of 6 nucleotide precursors 17 into the nascent strand 16, in order to avoid delays in the synthetic reaction due to the absence of a required nucleotide precursor 17.

Certain embodiments concern synthesis of a nascent strand 16 of DNA. The template strand 13 can be either RNA or DNA. With an RNA template strand 13, the synthetic reagent 15 may be a reverse transcriptase, examples of which are known in the art. In embodiments where the template strand 13 is a molecule of DNA, the synthetic reagent 15 may be a DNA polymerase, examples of which are known in the art.

In other embodiments, the nascent strand 16 can be a molecule of RNA. This requires that the synthetic reagent 15 be an RNA polymerase. In these embodiments, no primer 16 is required. However, the template strand 13 must contain a promoter sequence that is effective to bind RNA polymerase 15 and initiate transcription of an RNA nascent strand 16. The exact composition of the promoter sequence depends on the type of RNA polymerase 15 used. Optimization of promoter sequences to allow for efficient initiation of transcription is within the skill in the art. The embodiments are not limited as to the type of template molecule 13 used, the type of nascent strand 16 synthesized, or the type of polymerase 15 utilized. Virtually any template 13 and any polymerase 15 that can support synthesis of a nucleic acid molecule 16 complementary in sequence to the template strand 13 may be used.

In some alternative embodiments, the nucleotide precursors 17 may be chemically modified with a tag. The tag has a unique and highly visible optical signature that can be distinguished for each of the common nucleotide precursors 17. In certain embodiments, the tag may serve to increase the strength of the Raman emission signal or to otherwise enhance the sensitivity or specificity of the Raman detector 19 for nucleotide precursors 17. Non-limiting examples of tag molecules that could be used for embodiments involving Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine and aminoacridine. Other tag moieties that may be of use for particular embodiments include cyanide, thiol, chlorine, bromine, methyl, phosphorus and sulfur. In certain embodiments, carbon nanotubes may be of use as Raman tags. The use of tags in Raman spectroscopy is known in the art (e.g., U.S. Pat. Nos. 5,306,403 and 6,174,677). The skilled artisan will realize that Raman tags should generate distinguishable Raman spectra when bound to different nucleotide precursors 17, or different labels should be designed to bind only one type of nucleotide precursor 17.

In some embodiments, the tag exhibits an enhanced Raman signal. In alternative embodiments, tags that exhibit other types of signals, such as fluorescent or luminescent signals, may be employed. It is contemplated that alternative methods of detection may be used in such embodiments, for example fluorescence spectroscopy or luminescence spectroscopy. Many alternative methods of detection of nucleotide precursors 17 in solution are known in the art and may be used. For such methods, the Raman spectroscopic detector 19 may be replaced with a detector 19 designed to detect fluorescence, luminescence or other types of signals known in the art.

In certain embodiments, the template molecule 13 may be attached to a surface 14 such as functionalized glass, silicon, PDMS (polydimethlyl siloxane), silver or other metal coated surfaces, quartz, plastic, PTFE (polytetrafluoroethylene), PVP (polyvinyl pyrrolidone), polystyrene, polypropylene, polyacrylamide, latex, nylon, nitrocellulose, a glass bead, a magnetic bead, or any other material known in the art that is capable of having functional groups such as amino, carboxyl, thiol, hydroxyl or Diels-Alder reactants incorporated on its surface.

In some embodiments, functional groups may be covalently attached to cross-linking agents so that binding interactions between template strand 13 and polymerase 15 may occur without steric hindrance. Typical cross-linking groups include ethylene glycol oligomers and diamines. Attachment may be by either covalent or non-covalent binding. Various methods of attaching nucleic acid molecules 13 to surfaces 14 are known in the art and may be employed.

Definitions

As used herein, "a" or "an" may mean one or more than one of an item.

"Nucleic acid" 13 means either DNA, RNA, single-stranded, double-stranded or triple stranded and any chemical modifications thereof, although single-stranded nucleic acids 13 are preferred. Virtually any modification of the nucleic acid 13 is contemplated. As used herein, a single stranded nucleic acid 13 may be denoted by the prefix "ss", a double stranded nucleic acid by the prefix "ds", and a triple stranded nucleic acid by the prefix "ts."

A "nucleic acid" 13 may be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule 13.

A "nucleoside" is a molecule comprising a base (A, T, G, C or U) covalently attached to a pentose sugar such as deoxyribose, ribose or derivatives or analogs of pentose sugars.

A "nucleotide" refers to a nucleoside further comprising at least one phosphate group covalently attached to the pentose sugar. In some embodiments, the nucleotide precursors 17 are ribonucleoside triphosphates or deoxyribonucleoside triphosphates. It is contemplated that various substitutions or modifications may be made in the structure of the nucleotide precursors 17, so long as they are still capable of being incorporated into the nascent strand 16 by the polymerase 15. For example, in certain embodiments the ribose or deoxyribose moiety may be substituted with another pentose sugar or a pentose sugar analog. In other embodiments, the phosphate groups may be substituted by various groups, such as phosphonates, sulphates or sulfonates. In still other embodiments, the purine or pyrimidine bases may be substituted by other purines or pyrimidines or analogs thereof, so long as the sequence of nucleotide precursors 17 incorporated into the nascent strand 16 reflects the sequence of the template strand 13.

Nucleic Acids

Template molecules 13 may be prepared by any technique known to one of ordinary skill in the art. In certain embodiments, the template molecules 13 are naturally occurring DNA or RNA molecules, for example, chromosomal DNA or messenger RNA (mRNA). Virtually any naturally occurring nucleic acid 13 may be prepared and sequenced by the disclosed methods including, without limit, chromosomal, mitochondrial or chloroplast DNA or ribosomal, transfer, heterogeneous nuclear or messenger RNA. Nucleic acids 13 to be sequenced may be obtained from either prokaryotic or eukaryotic sources by standard methods known in the art.

Methods for preparing and isolating various forms of cellular nucleic acids 13 are known. (See, e.g., Guide to Molecular Cloning Techniques, eds. Berger and Kimmel, Academic Press, New York, N.Y., 1987; Molecular CloninP: A Laboratory Manual, 2nd Ed., eds. Sambrook, Fritsch and Maniatis, Cold Spring Harbor Press, Cold Spring Harbor, N.Y., 1989). Generally, cells, tissues or other source material containing nucleic acids 13 to be sequenced are first homogenized, for example by freezing in liquid nitrogen followed by grinding in a morter and pestle. Certain tissues may be homogenized using a Waring blender, Virtis homogenizer, Dounce homogenizer or other homogenizer. Crude homogenates may be extracted with detergents, such as sodium dodecyl sulphate (SDS), Triton X-100, CHAPS (3-[(3-cholamidopropyl)-dimethylammonio]-1-propane sulfonate), octylglucoside or other detergents known in the art. Alternatively or in addition, extraction may use chaotrophic agents such as guanidinium isothiocyanate, or organic solvents such as phenol. In some embodiments, protease treatment, for example with proteinase K, may be used to degrade cell proteins. Particulate contaminants may be removed by centrifugation or ultracentrifugation (for example, 10 to 30 min at about 5,000 to 10,000×g, or 30 to 60 min at about 50,000 to 100,000×g). Dialysis against aqueous buffer of low ionic strength may be of use to remove salts or other soluble contaminants. Nucleic acids 13 may be precipitated by addition of ethanol at −20° C., or by addition of sodium acetate (pH 6.5, about 0.3 M) and 0.8 volumes of 2-propanol. Precipitated nucleic acids 13 may be collected by centrifugation or, for chromosomal DNA, by spooling the precipitated DNA on a glass pipet or other probe.

The skilled artisan will realize that the procedures listed above are exemplary only and that many variations may be used, depending on the particular type of nucleic acid 13 to be sequenced. For example, mitochondrial DNA is often prepared by cesium chloride density gradient centrifugation, using step gradients, while mRNA is often prepared using preparative columns from commercial sources, such as Promega (Madison, Wis.) or Clontech (Palo Alto, Calif.). Such variations are known in the art.

The skilled artisan will realize that depending on the type of template nucleic acid 13 to be prepared, various nuclease inhibitors may be used. For example, RNase contamination in bulk solutions may be eliminated by treatment with diethyl pyrocarbonate (DEPC), while commercially available nuclease inhibitors may be obtained from standard sources such as Promega (Madison, Wis.) or BRL (Gaithersburg, Md.). Purified nucleic acid 13 may be dissolved in aqueous buffer, such as TE (Tris-EDTA) (ethylene diamine tetraacetic acid) and stored at −20° C. or in liquid nitrogen prior to use.

In cases where single stranded DNA (ssDNA) 13 is to be sequenced, a ssDNA 13 may be prepared from double stranded DNA (dsDNA) by standard methods. Most simply, dsDNA may be heated above its annealing temperature, at which point it spontaneously separates into ssDNA 13. Representative conditions might involve heating at 92 to 95° C. for 5 min or longer. Formulas for determining conditions to separate dsDNA, based for example on GC content and the length of the molecule, are known in the art. Alternatively, single-stranded DNA 13 may be prepared from double-stranded DNA by standard amplification techniques known in the art, using a primer that only binds to one strand of double-stranded DNA. Other methods of preparing single-stranded DNA 13 are known in the art, for example by inserting the double-stranded nucleic acid to be sequenced into the replicative form of a phage like M13, and allowing the phage to produce single-stranded copies of the template 13.

Although certain embodiments concern preparation of naturally occurring nucleic acids 13, virtually any type of nucleic acid 13 that can serve as a template for an RNA or DNA polymerase 15 could potentially be sequenced. For example, nucleic acids 13 prepared by various amplification techniques, such as polymerase chain reaction (PCRTM) amplification, could be sequenced. (See U.S. Pat. Nos. 4,683,195, 4,683,202 and 4,800,159.) Nucleic acids 13 to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts 13 may be isolated from vector DNA, for example, by excision with appropriate restriction endonucleases, followed by agarose gel electrophoresis and ethidium bromide staining. Selected size-fractionated nucleic acids 13 may be removed from gels, for example by the use of low melting point agarose or by electroelution from gel slices. Methods for insert isolation are known to the person of ordinary skill in the art.

Isolation of Single Nucleic Acid Molecules

In certain embodiments, the nucleic acid molecule 13 to be sequenced is a single molecule of ssDNA or ssRNA. A variety of methods for selection and manipulation of single ssDNA or ssRNA molecules 13 may be used, for example, hydrodynamic focusing, micro- manipulator coupling, optical trapping, or combination of these and similar methods. (See, e.g., Goodwin et al., 1996, Acc. Chem. Res. 29:607-619; U.S. Pat. Nos. 4,962,037; 5,405,747; 5,776,674; 6,136,543; 6,225,068.)

In certain embodiments, microfluidics or nanofluidics may be used to sort and isolate template nucleic acids 13. Hydrodynamics may be used to manipulate the movement of nucleic acids 13 into a microchannel, microcapillary, or a micropore. In one embodiment, hydrodynamic forces may be used to move nucleic acid molecules 13 across a comb structure 11 to separate single nucleic acid molecules 13. Once the nucleic acid molecules 13 have been separated, hydrodynamic focusing may be used to position the molecules 13. A thermal or electric potential, pressure or vacuum can also be used to provide a motive force for manipulation of nucleic acids 13. In exemplary embodiments, manipulation of template nucleic acids 13 for sequencing may involve the use of a channel block design incorporating microfabricated channels and an integrated gel material, as disclosed in U.S. Pat. Nos. 5,867,266 and 6,214,246.

In another embodiment, a sample containing the nucleic acid template 13 may be diluted prior to coupling to an immobilization surface 14. In exemplary embodiments, the immobilization surface 14 may be in the form of magnetic or non-magnetic beads or other discrete structural units. At an appropriate dilution, each bead will have a statistical probability of binding zero or one nucleic acid molecules 13. Beads with one attached nucleic acid molecule 13 may be identified using, for example, fluorescent dyes and flow cytometer sorting or magnetic sorting. Depending on the relative sizes and uniformity of the beads and the nucleic acids 13, it may be possible to use a magnetic filter and mass separation to separate beads containing a single bound nucleic acid molecule 13. In other embodiments, multiple nucleic acids 13 attached to a single bead or other immobilization surface 14 may be sequenced.

In alternative embodiments, a coated fiber tip 14 may be used to generate single molecule nucleic acid templates 13 for sequencing (e.g., U.S. Pat. No. 6,225,068). In other alternative embodiments, the immobilization surfaces 14 may be prepared to contain a single molecule of avidin or other cross-linking agent. Such a surface 14 could attach a single biotinylated primer 16, which in turn can hybridize with a single template nucleic acid 13 to be sequenced. This embodiment is not limited to the avidin-biotin binding system, but may be adapted to any coupling system known in the art.

In other alternative embodiments, an optical trap may be used for manipulation of single molecule nucleic acid templates 13 for sequencing. (E.g., U.S. Pat. No. 5,776,674). Exemplary optical trapping systems are commercially available from Cell Robotics, Inc. (Albuquerque, N. Mex.), S+L GmbH (Heidelberg, Germany) and P.A.L.M. Gmbh (Wolfratshausen, Germany).

Methods of Immobilization

In various embodiments, the nucleic acid molecules 13 to be sequenced may be attached to a solid surface 14 (or immobilized). Immobilization of nucleic acid molecules 13 may be achieved by a variety of methods involving either non-covalent or covalent attachment between the nucleic acid molecule 13 and the surface 14. In an exemplary embodiment, immobilization may be achieved by coating a surface 14 with streptavidin or avidin and the subsequent attachment of a biotinylated polynucleotide 13 (Holmstrom et al., Anal. Biochem. 209:278-283, 1993). Immobilization may also occur by coating a silicon, glass or other surface 14 with poly-L-Lys (lysine) or poly L-Lys, Phe (phenylalanine), followed by covalent attachment of either amino- or sulfhydryl-modified nucleic acids 13 using bifunctional crosslinking reagents (Running et al., BioTechniques 8:276-277, 1990; Newton et al., Nucleic Acids Res. 21:1155-62, 1993). Amine residues may be introduced onto a surface 14 through the use of aminosilane for cross-linking.

Immobilization may take place by direct covalent attachment of 5'-phosphorylated nucleic acids 13 to chemically modified surfaces 14 (Rasmussen et al., Anal. Biochem. 198:138-142, 1991). The covalent bond between the nucleic acid 13 and the surface 14 is formed by condensation with a water-soluble carbodiimide. This method facilitates a predominantly 5'-attachment of the nucleic acids 13 via their 5'-phosphates.

DNA 13 is commonly bound to glass by first silanizing the glass surface 14, then activating with carbodiimide or glutaraldehyde. Alternative procedures may use reagents such as 3-glycidoxypropyltrimethoxysilane (GOP) or aminopropyltrimethoxysilane. (APTS) with DNA 13 linked via amino linkers incorporated either at the 3' or 5' end of the molecule. DNA 13 may be bound directly to membrane surfaces 14 using ultraviolet radiation. Other non-limiting examples of immobilization techniques for nucleic acids 13 are disclosed in U.S. Pat. Nos. 5,610,287, 5,776,674 and 6,225,068.

The type of surface 14 to be used for immobilization of the nucleic acid 13 is not limiting. In various embodiments, the immobilization surface 14 may be magnetic beads, non-magnetic beads, a planar surface, a pointed surface, or any other conformation of solid surface 14 comprising almost any material, so long as the material is sufficiently durable and inert to allow the nucleic acid 13 sequencing reaction to occur. Non-limiting examples of surfaces 14 that may be used include glass, silica, silicate, PDMS, silver or other metal coated surfaces, nitrocellulose, nylon, activated quartz, activated glass, polyvinylidene difluoride (PVDF), polystyrene, polyacrylamide, other polymers such as poly(vinyl chloride), poly(methyl methacrylate) or poly(dimethyl siloxane), and photopolymers which contain photoreactive species such as nitrenes, carbenes and ketyl radicals capable of forming covalent links with nucleic acid molecules 13 (See U.S. Pat. Nos. 5,405,766 and 5,986,076).

Bifunctional cross-linking reagents may be of use in various embodiments, such as attaching a nucleic acid molecule 13 to a surface 14. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,311. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Synthetic Reagent

In certain embodiments, the sequencing reaction involves binding of a synthetic reagent 15, such as a DNA polymerase 15, to a primer molecule 16 and the catalyzed addition of nucleotide precursors 17 to the 3' end of the primer 16. Non-limiting examples of synthetic reagents 15 of potential use include DNA polymerases, RNA polymerases, reverse transcriptases, and RNA-dependent RNA polymerases. The differences between these synthetic reagents 15 in terms of their "proofreading" activity and requirement or lack of requirement for primers and promoter sequences are discussed herein and are known in the art. Where RNA polymerases are used as the synthetic reagent 15, the template molecule 13 to be sequenced may be double-stranded DNA.

In embodiments using synthetic reagents 15 with proofreading capability, the release of incorrectly incorporated nucleotide precursors 17 is detected by the detection unit 12, and the sequence data is accordingly corrected. In embodiments using synthetic reagents 15 without proofreading capability, errors are not corrected. These errors can be eliminated by sequencing both strands of the original template 13, or by sequencing multiple copies of the same strand 13. Non-limiting examples of polymerases 15 that could be used include Thematoga maritima DNA polymerase, AmplitaqFSm DNA polymerase, Taquenasem DNA polymerase, ThermoSequenasem, Taq DNA polymerase, Qbeta™ replicase, T4 DNA polymerase, Thermus themophilus DNA polymerase, RNA-dependent RNA polymerase and SP6 RNA polymerase.

A number of synthetic reagents 15 are commercially available, including Pwo DNA Polymerase from Boehringer Mannheim Biochemicals (Indianapolis, Ind.); Bst Polymerase from Bio-Rad Laboratories (Hercules, Calif.); IsoTherm™ DNA Polymerase from Epicentre Technologies (Madison, Wis.); Moloney Murine Leukemia Virus Reverse Transcriptase, P f i DNA Polymerase, Avian Myeloblastosis Virus Reverse Transcriptase, *Thermus flavus* (Tfl) DNA Polymerase and *Thermococcus litoralis* (ni) DNA Polymerase from Promega (Madison, Wis.); RAV2 Reverse Transcriptase, HIV-1 Reverse Transcriptase, T7 RNA Polymerase, T3 RNA Polymerase, SP6 RNA Polymerase, RNA Polymerase *E. coli, Thermus aquaticus* DNA Polymerase, T7 DNA Polymerase +/−3'35' exonuclease, Klenow Fragment of DNA Polymerase I, Thermus 'ubiquitous' DNA Polymerase, and DNA polymerase I from Amersham Pharmacia Biotech (Piscataway, N.J.). However, any synthetic reagent 15 that is known in the art for the template dependent polymerization of nucleotide precursors 17 may be used. (See, e.g., Goodman and Tippin, Nat. Rev. Mol. Cell. Biol. 1(2):101-9, 2000; U.S. Pat. No. 6,090,589.)

The skilled artisan will realize that the rate of polymerase 15 activity may be manipulated to coincide with the optimal rate of analysis of nucleotide precursors 17 by the detection unit 12. Various methods are known for adjusting the rate of polymerase 15 activity, including adjusting the temperature, pressure, pH, salt concentration, divalent cation concentration, or the concentration of nucleotide precursors 17 in the reaction chamber 11. Methods of optimization of polymerase 15 activity are known to the person of ordinary skill in the art.

Labels

Certain embodiments may involve incorporating a label into the nucleotide precursors 17, to facilitate their measurement by the detection unit 12. A number of different labels may be used, such as Raman tags, fluorophores, chromophores, radioisotopes, enzymatic tags, antibodies, chemiluminescent, electroluminescent, affinity labels, etc. One of skill in the art will recognize that these and other label moieties not mentioned herein can be used in the disclosed methods.

Labels for use in embodiments involving Raman spectroscopy are discussed above. In other embodiments, the label moiety to be used may be a fluorophore, such as Alexa 350, Alexa 430, AMCA (7-amino-4-methylcoumarin-3-acetic acid), BODIPY (5,7-dimethyl-4-bora-3a,4a-diaza-s-indacene-3-propionic acid) 630/650, BODIPY 650/665, BODIPY-FL (fluorescein), BODIPY-R6G (6-carboxyrhodamine), BODIPY-TMR (tetramethylrhodamine), BODIPY-TRX (Texas Red-X), Cascade Blue, Cy2 (cyanine), Cy3, Cy5,6-FAM (5-carboxyfluorescein), Fluorescein, 6-JOE (2'7'-dimethoxy-4'5'-dichloro-6-carboxyfluorescein), Oregon Green 488, Oregon Green 500, Oregon Green 514, Pacific Blue, Rhodamine Green, Rhodamine Red, ROX (6-carboxy-X-rhodamine), TAMRA (N,N,N',N'-tetramethyl-6-carboxyrhodamine), Tetramethylrhodamine, and Texas Red. Fluorescent or luminescent labels can be obtained from standard commercial sources, such as Molecular Probes (Eugene, Oreg.).

Primers

Primers 16 may be obtained by any method known in the art. Generally, primers 16 are between ten and twenty bases in length, although longer primers 16 may be employed. In certain embodiments, primers 16 are designed to be exactly complementary in sequence to a known portion of a template nucleic acid molecule 13, preferably close to the attachment site of the template 13 to the immobilization surface 14. Methods for synthesis of primers 16 of any sequence, for example using an automated nucleic acid synthesizer employing phosphoramidite chemistry are known and such instruments may be obtained from standard sources, such as Applied Biosystems (Foster City, Calif.) or Millipore Corp. (Bedford, Mass.).

Other embodiments, involve sequencing a nucleic acid 13 in the absence of a known primer binding site. In such cases, it may be possible to use random primers 16, such as random hexamers or random oligomers of 7, 8, 9, 10, 11, 12, 13, 14, 15 bases or greater length, to initiate polymerization of a nascent strand 16. To avoid having multiple polymerization sites on a single template strand 13, primers 16 besides those hybridized to the template molecule 13 near its attachment site to the immobilization surface 14 may be removed before initiating the synthetic reaction.

This could be accomplished, for example, by using an immobilization surface 14 coated with a binding agent, such as streptavidin. A complementary binding agent, such as biotin, could be attached to the 5' end of the primer molecules 16. After allowing hybridization between primer 16 and template 13 to occur, those primer molecules 16 that are not also bound to the immobilization surface 14 could be removed. Only those primers 16 that are hybridized to the template strand 13 will serve as primers 16 for template dependent DNA synthesis. In other alternative embodiments, multiple primer molecules 16 may be attached to the immobilization surface 14. A template molecule 13 is added and allowed to hydrogen bond to a complementary primer 16. A template dependent polymerase 15 then acts to initiate nascent strand 16 synthesis.

Other types of cross-linking could be used to selectively retain only one primer 16 per template strand 13, such as photoactivatable cross-linkers. As discussed above, a number of cross-linking agents are known in the art and may be used. Cross-linking agents may also be attached to the immobilization surface 14 through linker arms, to avoid the possibility of steric hindrance with the immobilization surface 14 interfering with hydrogen bonding between the primer 16 and template 13.

Reaction Chamber

The reaction chamber 11 is designed to hold the immobilization surface 14, nucleic acid template 13, primer 16, synthetic reagent 15 and nucleotide precursors 17 in an aqueous environment. In some embodiments, the reaction chamber 11 is designed to be temperature controlled, for example by incorporation of Pelletier elements or other methods known in the art. Methods of controlling temperature for low volume liquids used in nucleic acid polymerization are known in the art. (See, e.g., U.S. Pat. Nos. 5,038,853, 5,919,622, 6,054,263 and 6,180,372.)

In certain embodiments, the reaction chamber 11 and any associated fluid channels, for example, to provide connections to a molecule dispenser 21, to a waste port, to a template 13 loading port, or to a source of synthetic reagent 15 are manufactured in a batch fabrication process, as known in the fields of computer chip manufacture or microcapillary chip manufacture. In some embodiments, the reaction chamber 11 and other components of the apparatus 10, such as the molecule dispenser 21, may be manufactured as a single integrated chip. Such a chip may be manufactured by methods known in the art, such as by photolithography and etching. However, the manufacturing method is not limiting and other methods known in the art may be used, such as laser ablation, injection molding, casting, or imprinting techniques. Methods for manufacture of nanoelectromechanical systems may be used for certain embodiments, such as those employing a molecule dispenser 21. (See, e.g., Craighead, Science 290: 1532-36, 2000.) Microfabricated chips are commercially available from sources such as Caliper Technologies Inc. (Mountain View, Calif.) and ACLARA BioSciences Inc. (Mountain View, Calif.).

In a non-limiting example, Borofloat glass wafers (Precision Glass & Optics, Santa Ana, Calif.) may be pre-etched for a short period in concentrated HF (hydrofluoric acid) and cleaned before deposition of an amorphous silicon sacrificial layer in a plasma-enhanced chemical vapor deposition (PECVD) system (PEII-A, Technics West, San Jose, Calif.). Wafers may be primed with hexamethyldisilazane (HMDS), spin-coated with photoresist (Shipley 1818, Marlborough, Mass.) and soft-baked. A contact mask aligner (Quintel Corp. San Jose, Calif.) may be used to expose the photoresist layer with one or more mask designs, and the exposed photoresist removed using a mixture of Microposit developer concentrate (Shipley) and water. Developed wafers may be hard-baked and the exposed amorphous silicon removed using CF4 (carbon tetrafluoride) plasma in a PECVD reactor. Wafers may be chemically etched with concentrated HF to produce the reaction chamber 11 and any channels. The remaining photoresist may be stripped and the amorphous silicon removed.

Access holes may be drilled into the etched wafers with a diamond drill bit (Crystalite, Westerville, Ohio). A finished chip may be prepared by thermally bonding an etched and drilled plate to a flat wafer of the same size in a programmable vacuum furnace (Centurion VPM, J. M. Ney, Yucaipa, Calif.). In certain embodiments, the chip may be prepared by bonding two etched plates to each other. Alternative exemplary methods for fabrication of a reaction chamber 11 chip are disclosed in U.S. Pat. Nos. 5,867,266 and 6,214,246.

To facilitate detection of nucleotide precursors 17 by the detection unit 12, the material comprising the reaction chamber 11 may be selected to be transparent to electromagnetic radiation at the excitation and emission frequencies used for the detection unit 12. Glass, silicon, and any other materials that are generally transparent in the frequency ranges used for Raman spectroscopy, fluorescence spectroscopy, luminescence spectroscopy, or other forms of spectroscopy may be used for construction of the reaction chamber 11. In some embodiments the surfaces of the reaction chamber 11 that are opposite the detection unit 12 may be coated with silver, gold, platinum, copper, aluminum or other materials that are relatively opaque to the detection unit 12. In that position, the opaque material is available to enhance the Raman or other signal, for example by surface enhanced Raman spectroscopy, while not interfering with the function of the detection unit 12. In alternative embodiments, a mesh comprising silver, gold, platinum, copper or aluminum may be placed inside the reaction chamber.

In various embodiments, the reaction chamber 11 may have an internal volume of about 1 picoliter, about 2 picoliters, about 5 picoliters, about 10 picoliters, about 20 picoliters, about 50 picoliters, about 100 picoliters, about 250 picoliters, about 500 picoliters, about 1 nanoliter, about 2 nanoliters, 5 nanoliters, about 10 nanoliters, about 20 nanoliters, about 50 nanoliters, about 100 nanoliters, about 250 nanoliters, about 500 nanoliters, about 1 microliter, about 2 microliters, about 5 microliters, about 10 microliters, about 20 microliters, about 50 microliters, about 100 microliters, about 250 microliters, about 500 microliters, or about 1 milliliter.

Molecule Dispenser

The molecular dispenser 21 is designed to release the nucleotide precursors 17 into the reaction chamber 11. In certain embodiments, the molecule dispenser 21 may release each type of nucleotide precursor 17 in equal amounts. In such embodiments, a single molecule dispenser 21 may be used to release all four nucleotide precursors 17 into the reaction chamber 11. Other embodiments may require that the rate of release of the four types of nucleotide precursors 17 be independently controlled. In such embodiments, multiple molecule dispensers 21 may be used. In a non-limiting example, four separate molecule dispensers 21 may be used, each releasing a single type of nucleotide precursor 17 into the reaction chamber 11.

In various embodiments, the molecular dispenser 21 may be in the form of a pumping device. Pumping devices that may be used include a variety of micromachined pumps that are known in the art. For example, pumps having a bulging diaphragm, powered by a piezoelectric stack and two check valves are disclosed in U.S. Pat. Nos. 5,277,556, 5,271,724 and 5,171,132. Pumps powered by a thermopneumatic element are disclosed in U.S. Pat. No. 5,126,022. Piezoelectric peristaltic pumps using multiple membranes in series, or peristaltic pumps powered by an applied voltage are disclosed in U.S. Pat. No. 5,705,018. Published PCT Application No. WO 94/05414 discloses the use of a lamb-wave pump for transportation of fluid in micron scale channels. The skilled artisan will realize that the molecule dispenser 21 is not limited to the pumps disclosed herein, but may incorporate any design for the measured disbursement of very low volume fluids known in the art.

In other embodiments, the molecular dispenser 21 may take the form of an electrohydrodynamic pump (e.g., Richter et al., Sensors and Actuators 29:159-165 1991; U.S. Pat. No. 5,126,022). Typically, such pumps employ a series of electrodes disposed across one surface of a channel or reaction/pumping chamber. Application of an electric field across the electrodes results in electrophoretic movement of charged species in the sample. Indium-tin oxide films may be particularly suited for patterning electrodes on substrate surfaces, for example a glass or silicon substrate. These methods can also be used to draw nucleotide precursors 17 into the reaction chamber 11. For example, electrodes may be patterned on the surface of the molecule dispenser 21 and modified with suitable functional groups for coupling nucleotide precursors 17 to the surface of the electrodes. Application of a current between the electrodes on the surface of the molecule dispenser 21 and an opposing electrode results in electrophoretic movement of the nucleotide precursors 17 into the reaction chamber 11.

In certain embodiments, the molecular dispenser 21 may be designed to dispense a single nucleotide precursor 17 at a time. In other embodiments, the molecular dispenser 21 may be designed to dispense nucleotide precursors 17 in volumes of about 1 picoliter, about 2 picoliters, about 5 picoliters, about 10 picoliters, about 20 picoliters, about 50 picoliters, about 100 picoliters, about 250 picoliters, about 500 picoliters, about 1 nanoliter, about 2 nanoliters, 5 nanoliters, about 10 nanoliters, about 20 nanoliters, about 50 nanoliters, about 100 nanoliters, about 250 nanoliters, about 500 nanoliters, about 1 microliter, about 2 microliters, about 5 microliters, about 10 microliters, about 20 microliters or about 50 microliters Detection Unit Embodiments Involving Raman Spectroscopy In some embodiments, the detection unit 12 is designed to detect and quantify nucleotide precursors 17 by Raman spectroscopy. Various methods for detection of nucleotide precursors 17 by Raman spectroscopy are known in the art. (See, e.g., U.S. Pat. Nos. 5,306,403; 6,002,471; 6,174,677). Variations on surface enhanced Raman spectroscopy (SERS) or surface enhanced resonance Raman spectroscopy (SERRS) have been disclosed. In SERS and SERRS, the sensitivity of the Raman detection is enhanced by a factor of $10^6$ or more for molecules adsorbed on roughened metal surfaces, such as silver, gold, platinum, copper or aluminum surfaces.

A non-limiting example of a detection unit 12 is disclosed in U.S. Pat. No. 6,002,471. In this embodiment, the excitation beam 20 is generated by either a Nd:YAG laser 18 at 532 nm wavelength or a Tixapphire laser 18 at 365 nm wavelength. Pulsed laser beams 20 or continuous laser beams 20 may be used. The excitation beam 20 passes through confocal optics and a microscope objective, and is focused onto the reaction chamber 11. The Raman emission light from the nucleotide precursors 17 is collected by the microscope objective and the confocal optics and is coupled to a monochromator 19 for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 19. The detector 19 includes an avalanche photodiode interfaced with a computer for counting and digitization of the signal. In certain embodiments, a mesh comprising silver, gold, platinum, copper or aluminum may be included in the reaction chamber 11 to provide an increased signal due to surface enhanced Raman or surface enhanced Raman resonance.

Alternative embodiments of detection units 12 are disclosed, for example, in U.S. Pat. No. 5,306,403, including a Spex Model 1403 double-grating spectrophotometer 19 equipped with a gallium-arsenide photomultiplier tube (RCA Model C3 1034 or Burle Industries Model C3 103402) operated in the single-photon counting mode. The excitation source 18 is a 5 14.5 nm line argon-ion laser from Spectra-Physics, Model 166, and a 647.1 nm line of a krypton-ion laser (Innova 70, Coherent).

Alternative excitation sources 18 include a nitrogen laser (Laser Science Inc.) at 337 nm and a helium-cadmium laser (Liconox) at 325 nm (U.S. Pat. No. 6,174,677). The excitation beam 20 may be spectrally purified with a bandpass filter (Corion) and may be focused on the reaction chamber 11 using a 6× objective lens (Newport, Model L6×). The objective lens may be used to both excite the nucleotide precursors 17 and to collect the Raman signal, by using a holographic beam splitter (Kaiser Optical Systems, Inc., Model HB 647-26N18) to produce a right-angle geometry for the excitation beam 20 and the emitted Raman signal. A holographic notch filter (Kaiser Optical Systems, Inc.) may be used to reduce Rayleigh scattered radiation. Alternative Raman detectors 19 include an ISA HR-320 spectrograph equipped with a red-enhanced intensified charge-coupled device (RE-ICCD) detection system (Princeton Instruments). Other types of detectors 19 may be used, such as charged injection devices, photodiode arrays or phototransistor arrays.

Any suitable form or configuration of Raman spectroscopy or related techniques known in the art may be used for detection of nucleotides 16, 104, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Embodiments Involving FRET

In certain alternative embodiments, the nucleotide precursors 17 may be identified and quantified using fluorescence resonance energy transfer (FRET). FRET is a spectroscopic phenomenon used to detect proximity between a donor molecule and an acceptor molecule. The donor and acceptor pairs are chosen such that fluorescent emission from the donor overlaps the excitation spectrum of the acceptor. When the two molecules are associated (at a distance of less than 100 Angstroms), the excited-state energy of the donor is transferred non-radiatively to the acceptor and the donor emission is quenched. If the acceptor molecule is a fluorophore then its emission is enhanced. Compositions and methods for use of FRET with oligonucleotides are known in the art (e.g., U.S. Pat. No. 5,866,366).

Molecules that are frequently used as tags for FRET include fluorescein, 5-carboxyfluorescein (FAM), 2'7-dimethoxy-4'57-dichloro-6-carboxyfluorescein (JOE), rhodamine, 6-carboxyrhodamine (R6G), N,N,N7,N'-tetramethyl-6-carboxyrhodamine (TAMRA), 6-carboxy-X-rhodamine (ROX), 4-(4'-dimethylaminophenylazo) benzoic acid (DABCYL,), and 5-(2'-aminoethyl)aminonaphthalene-1-sulfonic acid (EDANS). Other potential FRET donor or acceptor molecules are known in the art (See U.S. Pat. No. 5,866,336, Table 1). The skilled artisan will be familiar with the selection of pairs of tag molecules for FRET (U.S. Pat. No. 5,866,336).

In embodiments involving FRET, the donor and acceptor molecules may be covalently or non-covalently attached to various constituents of the sequencing apparatus 10. In certain embodiments, the donor or acceptor molecules may be attached to the nucleotide precursors 17, to the template strand 13, or to the polymerase 15.

In certain embodiments, the donor molecule may be attached to the template strand 13 and the acceptor molecules attached to the nucleotide precursors 17. In this case, each type of nucleotide precursor 17 should be attached to an acceptor molecule with a distinguishable emission spectrum, while the donor molecule should be selected to have a broad emission spectrum that overlaps with the excitation spectra for all four of the acceptor molecules. Multiple donor molecules will be present on the template strand 13, for example in the form of fluorescent intercalating agents that insert into double-stranded nucleic acids. In alternative embodiments, the donor molecules may be covalently attached to the template strand 13, in a position that does not interfere with base pair formation. Upon excitation, the multiple donor molecules will transfer their energy to the acceptor tag molecules attached to the nucleotide precursors 17, resulting in an enhanced emission signal from the acceptor molecules. Because the strength of the signal enhancement decreases rapidly with distance, the greatest signal enhancement will occur for nucleotide precursors 17 that are incorporated into the nascent strand 16, while nucleotide precursors 17 that are free in solution within the reaction chamber 11 should show relatively weak signal enhancement. The wavelength of the excitation beam 20 may be selected to maximally excite the donor molecules, while only weakly exciting the acceptor molecules. In this case, only nucleotide precursors 17 that are incorporated into the nascent strand 16 will produce a detectable fluorescent signal. As each nucleotide precursor 17 is incorporated into the nascent strand 16, the signal from its donor tag will be detected.

In certain embodiments, the template nucleic acid 13 to be sequenced may be held within the field of view of a fluorescence microscope by methods known in the art, for example by use of an optical trap (e.g., U.S. Pat. No. 6,136,543). A non-limiting example of a fluorescence microscope that may be used is an inverted phase-contrast and incident-light fluorescence microscope (IMT2-RFC, Olympus Co., Ltd.), using an oil-immersed 100 power lens (Plan.multidot.Apochromat-.times. 100, 1.40 NA, Olympus Co., Ltd.) The excitation beam 20 may be emitted by a laser 18, as discussed above. Fluorescence emission may be collected through the objective lens, using appropriate filters, and detected using any sensitive fluorescence detector 19, such as a CCD device, photodiodes, photomultiplier tubes, or the equivalent.

In alternative embodiments, the donor molecule may be attached to the polymerase 15. As discussed above, each type of nucleotide precursor 17 should have a distinguishable acceptor molecule and the emission spectrum of the donor should overlap the excitation spectra of each of the acceptor molecules. Fluorescent detection may be performed as discussed in the embodiments involving a donor tagged template nucleic acid 13. Because the number of donor molecules will be substantially less than with the template 13 labeling method, the magnitude of signal enhancement for the acceptor molecules should be lower. However. in this embodiment the fluorescence resonance transfer should be limited to nucleotide precursors 17 that are either at or are close to the catalytic site of the polymerase 15. The donor molecule should be attached close to the catalytic site, but in a position where it will not interfere with the polymerase activity of the synthetic reagent 15. In this embodiment, a much less complicated FRET signal should be detected.

Information Processing and Control System and Data Analysis

In certain embodiments, the sequencing apparatus 10 may comprise an information processing and control system. The embodiments are not limiting for the type of information processing and control system used. An exemplary information processing and control system may incorporate a computer comprising a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments, the processor may be a Celeron®, an Itanium®, or a Pentium Xeon® processor (Intel Corp., Santa Clara, Calif.). In various other embodiments, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) and/or other static storage and a data storage device such as a magnetic disk or optical disc and its corresponding drive. The information processing and control system may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments, the detection unit 12 may also be coupled to the bus. Data from the detection unit 12 may be processed by the processor and the data stored in the main memory. Data on emission profiles for standard nucleotide precursors 17 may also be stored in main memory or in ROM. The processor may compare the emission spectra from nucleotide precursors 17 in the reaction chamber 11 to identify the type of nucleotide precursor 17 incorporated into the nascent strand 16. The main memory may also store the sequence of nucleotide precursors 17 disappearing from the reaction chamber 11. The processor may analyze the data from the detection unit 12 to determine the sequence of the template nucleic acid 13.

It is appreciated that a differently equipped information processing and control system than the example described above may be used for certain implementations. Therefore, the configuration of the system may vary in different embodiments. It should also be noted that, while the processes described herein may be performed under the control of a programmed processor, in alternative embodiments, the processes may be fully or partially implemented by any programmable or hardcoded logic, such as Field Programmable Gate Arrays (FPGAs), TTZ logic, or Application Specific Integrated Circuits (ASICs), for example. Additionally, the method may be performed by any combination of programmed general purpose computer components and/or custom hardware components.

Following the data gathering operation, the data will typically be reported to a data analysis operation. To facilitate the analysis operation, the data obtained by the detection unit 12 will typically be analyzed using a digital computer. Typically, the computer will be appropriately programmed for receipt and storage of the data from the detection unit 12, as well as for analysis and reporting of the data gathered. In certain embodiments, this may involve determining the concentration of nucleotide precursors 17 in the reaction chamber 11 from the Raman data and subtracting background Raman signals.

In certain embodiments, the information processing and control system may control the amount of nucleotide precursors 17 that are dispensed into the reaction chamber 11. In such embodiments, the information processing and control system may interface between the detection unit 12 and the molecule dispenser 21, to regulate the release of nucleotide precursors 17 by the molecule dispenser 21 to approximately match the rate of incorporation of nucleotide precursors 17 into the nascent strand 16.

In certain embodiments, custom designed software packages may be used to analyze the data obtained from the detection unit 12. In alternative embodiments, data analysis may be performed, using an information processing and control system and publicly available software packages. Non-limiting examples of available software for DNA sequence analysis include the PRISMm DNA Sequencing Analysis Software (Applied Biosystems, Foster City, Calif.), the Sequencherm package (Gene Codes, Ann Arbor, Mich.), and a variety of software packages available through the National Biotechnology Information Facility at website www.nbif.org/links/1.4.1.php.

What is claimed is:

1. An apparatus comprising:
    a reaction chamber to contain a polymerase and at least one nucleic acid template attached to an immobilization surface for growing a nascent strand complementary in sequence to the respective template;
    a detection unit comprising an excitation source, the detection unit being adapted for identifying and quantifying nucleotide precursors in the reaction chamber to identify nucleotide precursors incorporated into the nascent strand;
    a molecule dispenser for dispensing nucleotide precursors into the reaction chamber; and
    an information processing and control system operably coupled to the detection unit and the molecule dispenser, for controlling nucleotide precursor release rate from the dispenser to regulate the release of nucleotide precursors by the molecule dispenser to approximately match the rate of incorporation of nucleotide precursors into the nascent strand, wherein the molecule dispenser comprises multiple molecule dispensers for dispensing four types of nucleic acid precursors, whereby the rate of release of the four types of nucleotide precursors is independently controlled.

2. The apparatus of claim 1, wherein the reaction chamber contains a single nucleic acid molecule attached to an immobilization surface.

3. The apparatus of claim 1, wherein the reaction chamber contains a silver, gold, platinum, copper or aluminum mesh.

4. The apparatus of claim 1, further comprising a data storage unit.

5. The apparatus of claim 1, wherein the reaction chamber and molecule dispenser are part of an integrated chip.

6. The apparatus of claim 1, wherein the excitation source is a laser.

7. The apparatus of claim 1, wherein the Raman detector is a spectrometer or a monochromator.

* * * * *